United States Patent [19]

Phillipps et al.

[11] 3,983,111
[45] Sept. 28, 1976

[54] STEROIDAL ANAESTHETICS OF THE PREGNANE AND 19-NORPREGNANE SERIES

[75] Inventors: Gordon Hanley Phillipps, Wembley; Robin Lawrence, Stoke Poges; Christopher Earle Newall, Acton, all of England

[73] Assignee: Glaxo Laboratories Limited, Greenford, England

[22] Filed: Sept. 23, 1974

[21] Appl. No.: 508,650

Related U.S. Application Data

[63] Continuation of Ser. No. 356,115, May 1, 1973, abandoned.

[30] Foreign Application Priority Data
May 5, 1972 United Kingdom............... 21214/72

[52] U.S. Cl..................... 260/239.5; 260/239.55 R; 260/397.45; 260/349; 260/397.4
[51] Int. Cl.²........................................... C07J 41/00
[58] Field of Search.................. 260/239.5; 424/238; Machine Searched Steroids

[56] References Cited
UNITED STATES PATENTS

| | | | |
|---|---|---|---|
| 2,853,486 | 9/1958 | Sarett et al. ......................... | 260/349 |
| 3,272,708 | 9/1966 | Bertin et al....................... | 260/239.5 |
| 3,883,569 | 5/1975 | Phillipps et al. ........... | 260/239.55 R |

*Primary Examiner*—Elbert L. Roberts
*Attorney, Agent, or Firm*—Bacon & Thomas

[57] ABSTRACT

Steroid anaesthetics of the pregnane and 19-norpregnane series are described, the steroids having a 3α-hydroxy group, a 17α-hydrogen atom, a 20-oxo group and at the 21-position a cyano, azido or basic amino group.

28 Claims, No Drawings

STEROIDAL ANAESTHETICS OF THE PREGNANE AND 19-NORPREGNANE SERIES

This is a continuation, of application Ser. No. 356,115 filed May 1, 1973 and now abandoned.

This invention is concerned with compounds of the pregnane series having anaesthetic activity.

It has long been known that a number of steroids give rise to profound depression of the central nervous system and act pharmacodynamically as anaesthetics or hypnotics. Such compounds have been the subject of considerable study in an attempt to find anaesthetics to replace such substances as thiopentone sodium normally used but well known to be accompanied by some degree of hazard or disadvantage. The literature shows that very many steroid compounds have been studied in this regard. Reviews and discussions of some of the work carried out are to be found, for example, in "Methods in Hormone Research" (Edited by Ralph I. Dorfman, Vol. III Part A, Academic Press, London and New York, 1964, pages 415–475); H. Witzel, Z. Vitamin Hormon-Fermentforsch 1959, 10, 46–74; H. Selye, Endocrinology, 1942, 30, 437–453; S. K. Figdor et al., J. Pharmacol. Exptl. Therap., 1957, 119, 299–309 and Atkinson et al., J. Med. Chem. 1965, 8, 426–432.

A thorough review of the literature indicates that many anaesthetic steroids possess poor activty and/or long induction periods. A variety of undesired side effects such as paraesthesia and vein damage have also been noted.

We have now found useful anaesthetic activity in a new group of pregnane steroids.

Thus the invention provides steroids of the pregnane or 19-norpregnane series possessing a 3α-hydroxy group, a 17α-hydrogen atom, a 20-oxo group, and at the 21-position a cyano, basic amino or azido group, and the salts thereof.

The compounds of the invention may possess substituents at other positions of the steroid nucleus, for example at the 2, 3β, 11 or 16 positions. They may also be unsaturated, for example at the $\Delta^{8(9)}$ and/or $\Delta^1$ or $\Delta^4$ positions. When a hydrogen atom is present at the 5-position it may be in either the α or β configuration, preferably the α configuration.

In general, the compounds of the invention are good anaesthetics with generally short induction periods, the anaesthetic action at suitable doses being in general instantaneous; these compounds are thus excellent anaesthetics for inducing anaesthesia which is to be maintained e.g. by an inhalation anaesthetic such as ether, halothane, nitrous oxide, or trichloroethylene. The compounds are however capable of maintaining anaesthesia and analgesia to a sufficient degree to enable various surgical operations to be conducted without the aid of an inhalation anaesthetic, the required degree of anaesthesia being maintained if necessary by repeated administration (or even continuous administration). Moreover, the said anaesthetics in accordance with the invention in general give rise to minimal side-effects as compared to many previously described steroidal anaesthetics.

The basic amino group which may be present at the 21-position is preferably one in which the amino nitrogen atom is a member of a saturated or unsaturated, substituted or unsubstituted 3-8, preferably 5 or 6, membered ring which may contain one or more further hetero atoms such as nitrogen, oxygen or sulphur. The rings may be substituted for example by one or more oxo, alkyl (e.g. methyl), aralkyl, alkoxy, alkoxycarbonyl, or acyloxy groups. The ring preferably contains two hetero atoms (including the amino nitrogen atom), the second hetero atom being oxygen or sulphur. Saturated rings are generally preferred, examples being morpholine, thiamorpholine, and thiazolidine.

These latter rings, particularly morpholine, may themselves carry substituents, e.g. one or more alkyl groups having 1 to 6 carbon atoms such as methyl, particularly at the 3-position relative to the nitrogen atom.

Compounds having a morpholino group at the 21-position are particularly important, especially when an oxo group is also present at the 11-position.

Examples of substituents which may be present at the 2β-position include an acyloxy group having for example 1 to 9 carbon atoms, an ether or thioether group (i.e. the residue of an alcohol, a phenol or a thiol) containing for example 1–9 carbon atoms (e.g. methoxy), an alkyl or cycloalkyl group for example containing up to 9 carbon atoms, an aryl group (e.g. a phenyl group), an aralkyl group (e.g. a benzyl group), a hydroxy group, a thiocyanato group, a nitro-oxy group, or a halogen atom.

Acyloxy substituents (which may be saturated or unsaturated) include lower ($C_1$–$C_6$) alkanoyloxy groups, (substituted if desired, for example, with one or more halogen, e.g. chlorine atoms, lower alkoxy, amino or substituted amino groups), aroyloxy groups (e.g. a benzoyloxy group), or aralkanoyloxy groups (e.g. a phenylacetoxy group).

Ether substituents, which may be saturated or unsaturated, include lower ($C_1$–$C_6$) alkoxy groups, lower alkenyloxy groups (e.g. an allyloxy group), cycloalkoxy groups (e.g. a cyclohexyloxy group), aryloxy groups (e.g. a phenoxy group) and aralkoxy groups (e.g. a benzyloxy group). Thioether groups corresponding to the above-mentioned ether groups are representative of 2β-thioether substituents.

The 2β-substituent may alternatively be an azido, sulphonyloxy (e.g. tosyloxy) group or an acylthio group.

Examples of 2β-alkyl groups include especially lower alkyl groups containing 1–5 carbon atoms such as methyl, ethyl, propyl, butyl, isobutyl and t-butyl groups. An example of a cycloalkyl group is a cyclohexyl group.

Examples of lower alkanoyloxy 2β-substituents include acetoxy, propionyloxy, butyryloxy, piperidinoacetoxy, morpholinoacetoxy, diethylaminoacetoxy and chloroacetoxy groups. Examples of lower alkoxy groups include methoxy, ethoxy, propoxy, isopropoxy, n-butoxy and t-butoxy groups, and the corresponding thio compounds exemplify lower alkyl thio substituents.

Lower alkoxy and lower alkylthio substituents at the 2β-position may themselves be substituted for example by one or more halogen (e.g. chlorine) atoms, lower alkoxy, esterified carboxyl (e.g. ethoxycarbonyl), hydroxy, amino or substituted amino (e.g. morpholino) groups, or substituted or unsubstituted acyloxy (e.g. morpholinoacetoxy, chloroacetoxy or diethylaminoacetoxy), or heterocyclic groups, e.g. a tetrahydrofuranyl group. Alkyl, cycloalkyl and aryl groups may also be substituted.

The 2β-position may also carry amino substituents, e.g. amino or substituted amino groups, for example mono- or di-alkylamino or saturated, unsaturated or aromatic heterocyclic amino groups, e.g. a morpholino group.

A particularly important 2β-substituent is an ethoxy group.

Examples of substituents which may be present at the 2β-position are alkyl groups, e.g. having 1 to 6 carbon atoms such as methyl or ethyl, or halogen atoms, e.g. chlorine or bromine.

Examples of substituents which may be present at the 3β-position are alkyl groups, e.g. having 1 to 6 carbon atoms such as methyl, ethyl or pentyl.

An oxo group may be present at the 11-position and compounds having this substituent are particularly important. Alternatively, a hydroxy group may be present at the 11-position, in either the α configuration or, in the presence or absence of a ($C_{1-6}$) α-alkyl or alkenyl group (e.g. methyl or allyl), in the β configuration. Another possible grouping is an epoxy group linked also to the 9-position.

The 16-position may be substituted by one or more alkyl or alkoxy groups having 1 to 6 carbon atoms (e.g. methyl ethyl, methoxy, or gem-dimethyl) or by a halogen atom (e.g. fluorine or chlorine). A single 16-substituent may be in the α or β configuration.

Certain of the compounds of the invention, e.g. those containing a basic nitrogen atom, are capable of forming acid addition salts and this has the advantage of tending to improve the water solubility of the compounds. Such salts include, in the case of amino-substituted compounds, hydrochlorides, hydrobromides, phosphates, sulphates, p-toluenesulphonates, methanesulphonates, citrates, tartrates, acetates, ascorbates, lactates, maleates and succinates.

Solutions of acid addition salts of compounds containing a basic nitrogen atom may also dissolve further quantities of the free base. These solutions can be desirable in that they are less acid than those of the acid addition salt, and they may be formed for example by adding the free base or another base to a solution of the acid addition salt. For example, aqueous 3α-hydroxy-21-morpholino-5α-pregnane-11,20-dione citrate may dissolve up to 2 or more equivalents of the free base.

Compounds having a 21-cyano group are capable of forming water soluble salts, such as alkali metal, e.g. sodium, potassium or lithium, and ammonium (including substituted ammonium) salts.

When these salts are used as anaesthetics they should be non-toxic, i.e. physiologically acceptable in the dosage at which they are administered. Other salts may, however, be of use in for example, isolation of the product from a synthetic reaction.

Particularly preferred compounds in accordance with the invention by virtue of their excellent anaesthetic properties are:

1. 21-Cyano-3α-hydroxy-5α-pregnane-11,20-dione and its sodium salt;
2. 21-Cyano-2β-ethoxy-3α-hydroxy-5α-pregnane-11,20-dione and its sodium salt;
3. 21-Cyano-2β-methoxy-3α-hydroxy-5α-pregnane-11,20-dione;
4. 21-Cyano-2β-isopropoxy-3α-hydroxy-5α-pregnane-11,20-dione;
5. 21-Cyano-3α-hydroxy-16α-methyl-5α-pregnane-11,20-dione;
6. 3α-Hydroxy-21-morpholino-5α-pregnane-11,20-dione, and its citrate, mesylate and hydrochloride;
7. 2β-Ethoxy-3α-hydroxy-21-morpholino-5α-pregnane-11,20-dione and its citrate, phosphate, acetate and ascorbate;
8. 3α-Hydroxy-16α-methyl-21-morpholino-5α-pregnane-11,20-dione;
9. 3α-Hydroxy-21-(2'-methylmorpholino)-5α-pregnane-11,20-dione;
10. 3α-Hydroxy-21-(cis-2',6'-dimethylmorpholino)-5α pregnane-11,20-dione;
11. 3α-Hydroxy-21-thiamorpholino-5α-pregnane-11,20-dione;
12. 3α-Hydroxy-21-thiamorpholino-19-nor-5α-pregnane-11,20-dione and its citrate;
13. 21-Azido-3α-hydroxy-5α-pregnane-11,20-dione.
14. 21-Azido-2β-ethoxy-3α-hydroxy-5α-pregnane-11,20-dione;
15. 21-Azido-3α-hydroxy-5β-pregnane-11,20-dione;
16. 21-Azido-3α-hydroxy-5α-pregnan-20-one;
17. 21-Azido-3α-hydroxy-16α-methyl-5α-pregnane-11,20-dione;
18. 21-Azido-3α-hydroxy-2β-methoxy-5α-pregnan-20-one;
19. 21-Azido-3α-hydroxy-19-nor-5α-pregnane-11,20-dione;
20. 21-Azido-3α-hydroxy-5α-pregn-1-ene-11,20-dione;
21. 21-Cyano-3α-hydroxy-2β-methyl-5α-pregnane-11,20-dione;
22. 3α-Hydroxy-21-thiazolidino-5α-pregnane-11,20-dione; and
23. 21-Azido-3α-hydroxy-2β-methyl-5α-pregnane-11,20-dione.

Particularly preferred compounds in the above list are compounds 1, 2, 3, 6, 7, 8, 9, 10, 11 and 12 and their salts, 13, 14, 16, 18, 20, 21 and 22.

PHARMACEUTICAL FORMULATIONS

The anaesthetic compounds of the invention may be formulated as convenient, following generally known pharmaceutical practices, (including both human and veterinary medical practices), with the aid of one or more pharmaceutical carriers or excipients. For anaesthetic purposes, the steroids will be given by injection and thus one aspect of this invention comprises an anaesthetic composition for parenteral administration comprising an anaesthetic compound in accordance with the invention in a parenterally acceptable vehicle. When the anaesthetic compounds are sufficiently soluble in water (e.g. the salts, particularly the citrates referred to above) they may be formulated in aqueous solutions (e.g. isotonic sterile solutions). Many of the anaesthetic steroids of the invention are poorly soluble in water. We have found however that they may be formulated for parenteral administration in an aqueous solution of a parenterally acceptable non-ionic surface active agent. These surface active agents may also be used even where the steroid is sufficiently water soluble as they may reduce the risk of thrombophlebitis.

The non-ionic surface active agents used for the purpose of this invention are generally those of the water-soluble type, conveniently having an HLB value of at least 9, preferably at least about 12, advantageously at least about 13. Preferably the HLB value of the surface active agent is not greater than about 18. A mixture of surface agents may be used, in which case it is the HLB value of the mixture which is conveniently between the values just mentioned.

The surface active agent must naturally be one which is physiologically compatible, i.e. of itself give rise to no physiologically unacceptable side effects in the dosages employed in the intended species to be treated (man or animal).

Surface active agents for use in accordance with the invention are for example to be found among the following non-ionic surfactants and classes of surfactants:

Polyoxyethylated derivatives of fatty (C12–C20) glyceride oils, e.g. castor oil, containing from 35 to 60 oxyethylene groups per mole of fatty oil. Polyoxyethylene ethers (containing from 10 to 30 oxyethylene groups) of long chain alcohols (containing for example from 12–18 carbon atoms).

Polyoxyethylene-polyoxypropylene ethers containing from 5 to 150 and from 15 to 50 oxyethylene and oxypropylene groups respectively. Polyoxyethylene ethers (containing from 6 to 12 oxyethylene groups) of alkyl phenols the alkyl groups of which preferably contain 6–10 carbon atoms.

Polyoxyethylated (containing from 15 to 30 oxyethylene groups) fatty acid (e.g. C12–18) esters of sugar alcohol anhydrides e.g. sorbitan or mannitan.

Long-chain (e.g. C10–16) alkanoyl mono- and dialkanolamides (the alkanol portions of which for example contain 1–5 carbon atoms) for example lauroyl mono- and di-ethanolamides. Polyethylene glycol esters (containing from 6 to 40 ethylene oxide units) of long chain fatty acids (containing for example 12–18 carbon atoms) e.g. polyethyleneglycol monooleate (containing for example 8 ethylene oxide units).

Other useful surfactants include phospholipids such as lecithins, e.g. egg or soyabean lecithins.

Examples of non-ionic surface active agents, of the foregoing types, useful in accordance with the invention include:

Cremophor EL, a polyoxyethylated castor oil containing about 40 ethylene oxide units per triglyceride unit;

Tween 80, polyoxyethylene sorbitan monooleate containing about 20 ethylene oxide units;

Tween 60, polyoxyethylene sorbitan monostearate containng about 20 ethylene oxide units; and Tween 40, polyoxyethylene sorbitan monopalmitate containing about 20 ethylene oxide units.

The expression "solutions" is used herein to denote liquids which have the appearance of true solutions and are thus opticaly clear and capable of passage, for example through a micro-porous filter, irrespective of whether such solutions are true solutions in the classical chemical sense and irrespective of whether they are stable or metastable. Thus it may be that the steroid is associated with micelles. The solutions of this invention, irrespective of their precise physical nature, behave as true solutions for the practical purpose of intravenous injection.

The proportion of surface active agent to be used in the compositions of this invention depends upon its nature and upon the concentration of steroid desired in the final composition.

In preferred compositions according to the invention the proportion of surfactant is preferably at least 5% by weight and advantageously above 10% by weight. A very convenient proportion of surfactant has been found to be 20% by weight but 30% and up to 50% may be used. The proportions of surfactant are expressed by weight in relation to the total volume of the composition.

In one method of preparing the solutions comprising a surfactant, the steroid is first dissolved in the selected surfactant, for example with heating, and the resulting solution dissolved in water. Alternatively the steroid may be dissolved in a volatile organic solvent advantageously having a boiling point of less than about 80°C which is miscible with the surface active agent such as a volatile lower aliphatic ketone e.g. acetone or methyl ethyl ketone or a volatile halogenated hydrocarbon e.g. chloroform or methylene chloride. The surface active agent is then added to this solution, the organic solvent removed by evaporation, for example by passing a stream of an inert gas through the solution e.g. nitrogen and the resulting solution of steroid in surfactant is mixed with water.

The solutions may also be prepared by shaking the steroid with an aqueous solution of the surface active agent.

In all cases simple tests enable one to determine the relative proportions of surface active agent required.

As will be clear, the proportion of steroid which is dissolved in the aqueous medium according to the invention depends upon the water-solubility of the steroid and, where present, the nature and amount of surface active agent used. The composition will generally contain at least 1 mg/ml of steroid but solutions can be made containing for example up to 300 mg/ml of steroid or even 400 mg/ml. The more concentrated solutions can usually only be made with the watersoluble steroids, but solutions of adequate concentrations can also be peapred in cases where it is necessary to use a surfactant. In particular, we have surprisingly found that solutions can be prepared containing up to 30 mg/ml of water insoluble compounds containing both 21-azide and 11-oxo groups.

The anaesthetic solutions according to the invention are generally administered by intravenous injection although as is known in the anaesthetic art in certain cases, e.g. with young children, intramuscular injection might be preferred.

As is usual in the case of anaesthetics, the quantity of steroid used to induce anaesthesia depends upon the weight of the individual to be anaesthetised. For intravenous administration in the average man a dose of from 0.1 to 30 (e.g. 0.2 to 30) mg/kg will in general be found to be satisfactory to induce anaesthesia, the preferred dose being within the range of from 0.5 to 20 mg/kg. The dose will naturally vary to some extent dependent upon the physical condition of the patient, and the degree and period of anaesthesia required, all as is well known in the art. It is thus possible by adjustment of the dose to achieve durations of anaesthesia varying from about 10 minutes to up to an hour or more. If it is desired to maintain prolonged anaesthesia, repeated doses of the solutions of this invention may be used, such repeated doses being generally either of the same order or lower than the original dose. Alternatively continuous administration may be undertaken at for example a rate of 0.025–2.0 (e.g. 0.09 – 1.4) mg/kg/min.

Where the anaesthetic solutions are administered intramuscularly, higher doses are generally necessary.

COMPOUND PREPARATION

The compounds of the invention may in general be prepared by the nucleophilic displacement of a readily eliminatable substituent at the 21-position of a corresponding steroid whereby the desired 21-substituent is introduced.

The starting 21-substituted steroid is preferably the corresponding 21-bromo steroid, but other compounds may be used, for example a corresponding 21-chloro, 21-iodo or 21-sulphonyloxy (e.g. methanesulphonyloxy) compound.

In the preparation of the 21-cyano compounds, the corresponding 21-bromo compound may be reacted with a source of cyanide ions, for example a salt of hydrogen cyanide with an organic or inorganic base, preferably an alkali metal cyanide such as sodium or potassium cyanide. The cyanide is desirably present in excess. The reaction may be carried out in any suitable inert solvent (e.g. an alkanol such as ethanol or methanol, a ketone such as acetone or methyl ethyl ketone, nitrile solvents such as acetonitrile or amide solvents such as dimethylformamide or dimethylacetamide often advantageously in the presence of water). The reaction may be effected at any suitable temperature up to reflux. The initial reaction product is normally a salt of the desired nitrile with cations from the cyanide reactant and this is readily soluble in the reaction mixture and thus rather difficult to isolate. It is therefore preferable to add acid and isolate the product as the desired non-ionic nitrile.

In the preparation of the 21-amino compounds, the corresponding 21-bromo steroid may be reacted with an amine, for example an amine in which the amino nitrogen atom is a member of a 3-8 membered ring such as described above or is of the formula $HNR^1R^2$ where $R^1$ and $R^2$ are as defined above. The amine is desirably present in excess and indeed may be used as the reaction solvent. The reaction may alternatively be carried out in any suitable inert solvent (e.g. a cyclic ether such as tetrahydrofuran or dioxan, a ketone such as acetone or cyclohexanone, an amide such as dimethylformamide or diemthylacetamide, or an alcohol such as ethanol or methanol) at any suitable temperature up to reflux. The reaction may if desired be carried out under an atmosphere of nitrogen or in the presence of an acid binding agent such as calcium oxide, carbonate or bicarbonate.

In the preparation of 21-azido compounds the corresponding 21-bromo steroid may be reacted with a source of azide ions e.g. an alkali metal azide such as sodium or lithium azide. The reaction is preferably effected in a polar solvent medium (e.g. a cyclic ether such as dixoan or tetrahydrofuran, an amide or alcohol solvent such as referred to above, or dimethylsulphoxide, with or without a solvent for the steroid such as a halogenated hydrocarbon such as chloroform) at any suitable temperature up to reflux.

In these reactions, as indicated above the starting compound may instead carry another eliminatable 21-substituent instead of the bromine atom.

The 21-substituted compounds used as starting materials in the preparation of the compounds of the invention may readily be prepared from known compounds by conventional methods. A 21-bromo compound, for example, may be prepared by bromination of the corresponding 21-unsubstituted compound, for example with molecular bromine in a solvent such as methanol or ethanol. The reaction is preferably effected at a temperature of −10 to +30°C. If desired, the reaction may be accelerated by the presence of a catalyst such as hydrogen bromide (in acetic acid) or acetyl chloride.

In the preparation of compounds in accordance with the invention possessing an optional substituent or a carbon-carbon double bond such as described above, it is convenient for this substituent or unsaturation to be present in the 21-substituted starting material. Alternatively these substituents or unsaturation may be introduced subsequently, for example by generally known techniques using known compounds as starting materials. For convenience a number of methods of introducing the desired substituents or unsaturation into a 3-oxygenated-20-oxo-pregnane are set out below; certain of these methods are new.

Substitution at the 2β-position can be effected for example by way of the corresponding 2α,3α-epoxy compound. The epoxy compound itself may be prepared by first dehydrating a 3-hydroxy compound to give the corresponding $\Delta^2$ compound (e.g. by first tosylating the hydroxy group and then detosylating the product), and then treating the $\Delta^2$ compound with a peracid to form the 2α,3α epoxide ring.

A 2β-substituent may then be introduced by the method described in U.S. Pat. application Ser. No. 197915, now U.S. Pat. No. 3,869,451. This general method may be used to introduce all the 2β-substituents described above.

Methods for introducing substituents at the 2α, 3β, 11 and 16 positions are described in U.S. Pat. application Ser. Nos. 208959, now abandoned in favor of an allowed pending continuation thereof Ser. No. 443,451, filed Feb. 19, 1974, and 194918 now U.S. Pat. No. 3,825,565. These or analogous methods may be used to introduce all the substituents referred to above at these positions. For example, an 11-alkenyl or 16-alkyl group may be introduced by methods analogous to those described in U.S. Pat. application Ser. No. 208959 for the introduction of an 11-allyl or 16-methyl substituent.

5α-Steroids possessing $\Delta^1$ unsaturation may also be prepared by known methods, but we prefer to use a method which comprises converting a 2β-bromo-3α-hydroxy pregnane into its corresponding 2β,21-dibromo compound, if desired protecting the 3α-hydroxy group (e.g. as its tetrahydropyranyl ether), dehydrobrominating to give the $\Delta^1$ compound, and then deprotecting the product where necessary to give the desired 1,2-dehydro-3α-hydroxy-20-oxo-21-bromo compound.

The dehydrobromination may be effected, for example using a nitrogen containing Lewis base such as a di-lower alkyl lower acylamide e.g. dimethylformamide or dimethylacetamide advantageously in the presence of an alkali metal or alkaline earth metal carbonate, for example calcium carbonate.

In general it has been found convenient to effect the dehydrobromination at an elevated temperature for example from 80° to 170°C. Lower temperatures may be employed when a lithium or calcium halide is present.

Compounds possessing $\Delta^4$ unsaturation may be prepared from $\Delta^3$-steroids by methods analogous to those described for obtaining the $\Delta^1$ compounds from $\Delta^2$ steroids. Alternatively, $\Delta^4$-steroids may be obtained by the methods described in U.S. Pat. application Ser. No. 194918.

Compounds having a double bond between the 8- and 9-positions and an 11-oxo group may be prepared for example by the method described in U.S. Pat. application Ser. No. 208959. These compounds may also be prepared by dehydration of the corresponding 9α-hydroxy compound, for example using thionyl chloride in pyridine.

5α-Steroids of the invention may also be prepared from the corresponding 3-oxo compounds by stereospecific reduction, e.g. by the method of *Browne and Kirk* (J. Chem. Soc. C, 1969, 1653) or by the method of our U.S. Pat. application Ser. No. 305246, now U.S. Pat. No. 3,822,298. The latter method preferably uses a pre-formed iridium catalyst reduction system. For example, a reduction system may be prepared from an iridium acid or salt (e.g. chloroiridic acid), trivalent phosphorus compound such as a phosphorous acid ester (e.g. trimethyl phosphite), water and an organic reaction medium (e.g. an alcohol such as isopropanol). The reduction system is then neutralised (e.g. to a pH of 6 to 8.5) with an organic base such as a secondary or tertiary amine (e.g. triethylamine) and reacted with the steroid. When the catalyst system is preformed by heating at reflux for 16 to 72 hours, the reduction can be accomplished in 2–3 hours at reflux; longer times may be necessary at room temperature.

5β-Steroids may similarly be prepared by hydride reduction of 3-oxo steroids.

In the preparative methods described above, it may be desirable to protect a 3α-hydroxy or 20-oxo group during the reaction, the protection being subsequently removed to regenerate the hydroxy or oxo group. A 3α-hydroxy group may for example be protected in the form of a nitrate ester or a tetrahydropyranyl ether. A 20-oxo group may be protected as a ketal and regenerated for example by hydrolysis in the presence of an acid (e.g. hydrochloric or acetic) at a temperature of 0°–100°C.

The following Examples are given by way of illustration only.

All temperatures are in degrees Celsius. Ultra violet spectra were measured in ethanol. Optical rotations were measured in chloroform at approximately 1% w/v concentration unless stated otherwise. 'Petrol' refers to petroleum ether (b.p. 60°–80°). Preparative thin layer chromatography (preparative t.l.c.) was carried out in silica gel.

Three general methods, Methods A, B and C, were used in accordance with the invention to prepare a number of cyano, azido and amino compounds respectively. These methods were as follows:

METHOD A

Preparation of 21-cyano-3α-hydroxypregnan-20-ones

The appropriate 21-bromo-3α-hydroxypregnan-20-one in ethanol was treated with potassium cyanide and water. The solution was heated under reflux for 30 minutes, cooled, treated with 2N HCl and extracted into ethyl acetate. The organic layer was washed with water, dried ($Na_2SO_4$) and evaporated. The residue was purified by preparative t.l.c. and/or crystallisation to afford the required product.

METHOD B

Preparation of 21-azido-3α-hydroxypregnan-20-ones

A solution of the appropriate 21-bromo-3α-hydroxypregnan-20-one in methanol was added to a solution of lithium azide in methanol. The mixture was refluxed for two hours and then partitioned between water and ether. The organic layer was washed with water, dried ($Na_2SO_4$) and evaporated. The residue was purified by preparative t.l.c. and/or crystallisation to give the required product.

METHOD C

Preparation of 21-amino-3α-hydroxypregnan-20-ones

A solution of a mixture of the appropriate 21-bromo-3α-hydroxypregnan-20-one and amine in dry tetrahydrofuran was refluxed. The resulting solution was partitioned between water and ether. The organic layer was washed with water, dried and evaporated. The residue was subjected to preparative t.l.c. to give the pure product.

Method A was used to prepare the following compounds:

| Ex. No. | Compound |
|---|---|
| 1 | 21-cyano-3α-hydroxy-5α-pregnane-11,20-dione |
| 2 | 21-cyano-2β-ethoxy-3α-hydroxy-5α-pregnane-11,20-dione |
| 3 | 21-cyano-3α-hydroxy-5β-pregnane-11,20-dione |
| 4 | 21-cyano-3α-hydroxy-5α-pregnan-20-one |
| 5 | 21-cyano-3α-hydroxy-2β-methoxy-5α-pregnane-11,20-dione |
| 6 | 21-cyano-3α-hydroxy-2β-iso-propoxy-5α-pregnane-11,20-dione |
| 7 | 21-cyano-3α-hydroxy-2β-n-propoxy-5α-pregnane-11,20-dione |
| 8 | 21-cyano-3α-hydroxy-16α-methyl-5α-pregnane-11,20-dione |
| 9 | 21-cyano-3α-hydroxy-5α-pregn-1-ene-11,20-dione |
| 10 | 21-cyano-3α-hydroxy-2β-methyl-5α-pregnane-11,20-dione |

Details of the methods used in these examples and some properties of the compounds are shown in Table 1 which follows.

The column headed "Conc" in Table I (and in Tables II and III below) shows the concentration (% w/v) at which the optical rotations were measured. The following abbreviations are used in Tables I–III:

| EA | = | ethyl acetate | CH | = | cyclohexane |
|---|---|---|---|---|---|
| MA | = | methyl acetate | P | = | petrol |
| B | = | benzene | THF | = | tetrahydrofuran |
| A | = | acetone | | | |

TABLE I

| | | | | | | | | | | |
|---|---|---|---|---|---|---|---|---|---|---|
| | 21-Cyano compounds prepared by Method A | | | | | | | | | |
| Ex. No. | Wt. of 21-Bromo Compound (mg.) | Wt of KCN (mg) | Vol of EtOH (ml) | Vol of $H_2O$ (ml) | Eluting Solvent | Crystallisation Solvent | Yield (mg) | M. pt. °C | $[\alpha]_D$ | Conc. |
| 1 | 1.0 g | 325 | 60 | 5 | EA/CHCl₃ 1:1 | B/CH | 158 | 158 | +96 | 1.0 |
| 2 | 2.0 g | 650 | 120 | 10 | EA/P 1:1 & 2:1 | A/P | 600 | 184 | +103 | 0.9 |
| 3 | 1.0 g | 325 | 60 | 5 | — | A | 300 | 218 | +101 | 1.1 |
| 4 | 1.0 g | 325 | 60 | 5 | — | A | 600 | 209–211 | +116 | 0.5 |

TABLE I-continued

| | | 21-Cyano compounds prepared by Method A | | | | | | | | |
|---|---|---|---|---|---|---|---|---|---|---|
| Ex. No. | Wt. of 21-Bromo Compound (mg.) | Wt of KCN (mg) | Vol of EtOH (ml) | Vol of H₂O (ml) | Eluting Solvent | Crystallisation Solvent | Yield (mg) | M. pt. °C | $[\alpha]_D$ | Conc. |
| 5 | 436 | 130 | 22 | 2 | EA/P 1:1 | A/P | 250 | 210 | +109 | 1.2 |
| 6 | 430 | 130 | 22 | 2 | EA/P 1:1 | A/P | 100 | 174 | +94 | 1.0 |
| 7 | 1.15 g | 325 | 60 | 5 | EA/P 2:1 | A/P | 300 | 219 | +74 | 1.0 |
| 8[1] | 1.0 g | 330 | 60 | 5 | EA/CHCl₃ 1:1 | — | 480 | — | +96 | 1.0 |
| 9 | 300 | 97.5 | 20 | 1.5 | EA/CHCl₃ 1:1 | — | 100 | — | +58 | 0.6 |
| 10[2] | 240 | 100 | 40 | 2 | EA/P 1:1 | — | 150 | | +110 | 1.0 |

[1]The resulting solution after reflux was not treated with 2N HCl.
[2]Solution was refluxed for 1 hour.

Method B was used to prepare the following compounds:

| Ex. No. | Compound |
|---|---|
| 11 | 21-azido-3α-hydroxy-3β-methyl-5α-pregnane-11,20-dione |
| 12 | 21-azido-3α-hydroxy-16α-methyl-5α-pregnane-11,20-dione |
| 13 | 21-azido-3α-hydroxy-5α-pregn-1-ene-11,20-dione |
| 14 | 21-azido-3α-hydroxy-5α-pregnane-11,20-dione |
| 15 | 21-azido-2β-ethoxy-3α-hydroxy-5α-pregnane-11,20-dione |
| 16 | 21-azido-3α-hydroxy-5β-pregnane-11,20-dione |
| 17 | 21-azido-3α-hydroxy-5α-pregnan-20-one |
| 18 | 21-azido-3α-hydroxy-2β-methoxy-5α-pregnan-20-one |
| 19 | 21-azido-3α-hydroxy-19-nor-5α-pregnane-11,20-dione |
| 20 | 21-azido-3α-hydroxy-2β-methyl-5α-pregnane-11,20-dione |

Details of the methods used in these examples and some properties of the compounds are shown in Table II which follows.

Method C was used to prepare the following compounds:

| Ex. No. | Compound |
|---|---|
| 21 | 3α-hydroxy-21-morpholino-5β-pregnane-11,20-dione |
| 22 | 3α-hydroxy-3β-methyl-21-morpholino-5α-pregnane-11,20-dione |
| 23 | 3α-hydroxy-21-morpholino-19-nor-5α-pregnane-11,20-dione |
| 24 | 3α-hydroxy-16α-methyl-21-morpholino-5α-pregnane-11,20-dione |
| 25 | 3α-hydroxy-21-morpholino-5α-pregn-1-ene-11,20-dione |
| 26 | 3α-hydroxy-21-thiamorpholino-5α-pregnane-11,20-dione |
| 27 | 3α-hydroxy-21-thiamorpholino-19-nor-5α-pregnane-11,20-dione |
| 28 | 3α-hydroxy-21-(2'-methylmorpholino)-5α-pregnane-11,20-dione |
| 29 | 3α-hydroxy-2β-methoxy-21-morpholino-5α-pregnan-20-one |
| 30 | 3α-hydroxy-21-(3'-pyrrolin-1'-yl)-5α-pregnane-11,20-dione |
| 31 | 3α-hydroxy-21-pyrrolidino-5α-pregnane-11,20-dione |
| 32 | 3α-hydroxy-21-piperidino-5α-pregnane-11,20-dione |
| 33 | 2β-ethoxy-3α-hydroxy-21-morpholino-5α-pregnane- |

TABLE II

| | | 21-Azido compounds prepared by Method B | | | | | | | | |
|---|---|---|---|---|---|---|---|---|---|---|
| Ex. NO. | Wt. of 21-Bromo compound (mg.) | Vol of MeOH (ml) | Wt. of LiN₃ (mg) | Vol of MeOH (ml) | Eluting Solvent | Crystallisation Solvent | Yield (mg) | M. pt. °C | $[\alpha]_D$ | Conc. |
| 11[2] | 700 | 20 | 250 | 100 | CHCl₃ | MA/P | 400 | 176 | +141 | 0.8 |
| 12[2] | 750 | 20 | 250 | 100 | B/EA 2.5:1 | — | 200 | — | +98 | 0.9 |
| 13 | 300 | 8 | 125 | 40 | B/EA 2.5:1 | — | 100 | — | +81 | 0.4 |
| 14 | 750 | 20[1] | 250 | 100 | EA/P 1:2 | — | 550 | — | +106 | 1.0 |
| 15 | 1.0g | 20[1] | 325 | 150 | EA/P 1:1 | — | 330 | — | +94.8 | 1.0 |
| 16[3] | 1.0g | 30[1] | 325 | 150 | EA/P 1:1 | — | 575 | — | +120.8 | 1.0 |
| 17[3] | 1.0g | 30[1] | 325 | 150 | — | A/P | 400 | 150 | +126 | 1.0 |
| 18[2] | 1.0g | — | 130 | 150 | EA/CHCl₃ 1:1 | MA/P | — | 162-64 | — | — |
| 19[4] | 794 | 30[1] | 260 | 100 | CHCl₃ | A/P (twice) | 195 | 142-144 | +219 | 1.2 |
| 20[2,3,5] | 200 | — | 75 | 100 | EA/P 1:1 | — | 52 | — | +110 | 0.4 |

[1]Methanol was replaced by chloroform.
[2]After reflux, the solution was evaporated to small volume before partition between water and ether.
[3]The mixture was refluxed for 1½ hours.
[4]The extracting solvent was ethyl acetate.
[5]The mixture was refluxed for 3 hours.

-continued

| Ex. No. | Compound |
|---|---|
| | 11,20-dione |
| 34 | 3α-hydroxy-2β-methyl-21-morpholino-5α-pregnane-11,20-dione |
| 35 | 3α-hydroxy-21-thiazolidino-5α-pregnane-11,20-dione |

Details of the methods used in these examples and some properties of the compounds are shown in Table III below.

TABLE III

21-Amino compounds prepared by Method C

| Ex. No. | Wt. of 21-Bromo compound (mg) | Vol of amine (ml) | Vol of THF (ml) | Eluting Solvent | Yield (mg) | $[\alpha]_D°$ | Conc | Reaction Time (hrs) |
|---|---|---|---|---|---|---|---|---|
| 21[1] | 1.0g | 4.5 | 25 | EA/A 1:1 | 355 | +76.7 | 1.0 | 2 |
| 22 | 700 | 4 | 40 | EA | 400 | +71 | 1.1 | 4 |
| 23[1,2] | 794 | 870 mg | 20 | EA | 310 | +137 | 1.1 | 1.25 |
| 24 | 1.0g | 4.5 | 42 | EA | 600 | +65 | 1.1 | 4 |
| 25 | 800 | 4 | 40 | EA | 400 | +43 | 1.3 | 4 |
| 26[2,3] | 1.0g | 720 mg | 40 | EA/P 1:1 | 560 | +74 | 1.3 | 2/3 |
| 27[4] | 800 | 400 mg | 40 | EA/P 1:1 | 391 | +120 | 1.75 | 2 |
| 28[5] | 1.6g | 0.7 | 40 | CHCl$_3$:EA 1:2 | 900 | +75 | 1.4 | 2 |
| 29 | 1.0g | 4 | 25 | EA | 800 | +74 | 1.0 | 4 |
| 30 | 1.0g | 0.5 | 30[6] | EA/CHCl$_3$ 1:1 | | +82 | 1.4 | 2 |
| 31[8] | 750 | 1.5 | 30 | — | 500 | +77 | 1.3 | 3 |
| 32 | 750 | 1.5 | 30 | — | 500 | +82 | 1.0 | 3 |
| 33 | 2.0g | 4 | 60[6,7] | EA/CHCl$_3$/A 1:1:1 | 500 | +71 | 0.7 | 16 |
| 34[1,2] | 240 | 0.2 | 40 | EA | 169 | +99 | 0.9 | 1 |
| 35[2] | 1.0g | 0.5 | 40[6] | EA/P 1:1 | 170 | +67 | 0.42 | 1.5 |

[1]The reaction mixture was treated with 5% NaHCO$_3$ before extraction.
[2]Ethyl acetate replaced ether as the extraction solvent.
[3]The ethyl acetate extract was washed with 5% NaHCO$_3$.[4]After refluxing for 2 hours a further 0.1ml. of thiamorpholine was added and the reaction was continued for a further hour. hour.
[5]After refluxing, the reaction solution was left overnight at room temperature.
[6]T.H.F. was replaced by acetone.
[7]The reaction was carried out at room temperature.
[8]The product was purified by recrystallisation from acetone/petrol.

6. T.H.F. was replaced by acetone.

A solution of 21-cyano-3α-hydroxy-5α-pregnane-11,20-dione (80 mg, 0.222 mmole) in ethanol (4.4 ml) was treated with 0.1N sodium hydroxide solution (2.22 ml, 0.222 mmole). The solvents were then slowly removed under reduced pressure at room temperature and water (8 ml) added to afford an aqueous solution of title compound of concentration 10 mg. ml$^{-1}$ with respect to steroid (pH 11.7).

EXAMPLE 37

21-Cyano-2β-ethoxy-3α-hydroxy-5α-pregnane-11,20-dione sodium salt

A solution of 21-cyano-2β-ethoxy-3α-hydroxy-5α-pregnane-11,20-dione (80 mg, 0.2 mmole) in ethanol (4.4 ml) was treated with 0.1N-sodium hydroxide solution (2.0 ml, 0.2 mmole). The solution was evaporated slowly under reduced pressure at room temperature to constant weight. The residue was dissolved in sufficient water (8 ml) to make the concentration of the aqueous solution 10 mg.ml$^{-1}$ with respect to steroid (pH 11.3).

EXAMPLE 38

3α-Hydroxy-21-morpholino-5α-pregnane-11,20-dione

A solution of 21-bromo-3α-hydroxy-5α-pregnane-11,20-dione (1.6 g) in refluxing tetrahydrofuran (40 ml) was treated with morpholine (0.7 ml) under nitrogen for 3 hr and then poured into ether. The ethereal solution was washed successively with 5% aqueous sodium bicarbonate and water, dried (Na$_2$SO$_4$) and evaporated. The residue was partitioned between a mixture of 2N-hydrochloric acid (6 ml), water (200 ml), acetone (20 ml) and methylene chloride (120 ml). The aqueous phase was treated with 2N-sodium hydroxide (6 ml) and sodium chloride (20 g) and the resulting mixture was extracted with methylene chloride. The extracts were washed with water, dried (Na$_2$SO$_4$) and evaporated to give title compound (1.5 g) as a white foam, $[\alpha]_D + 81°$ (c 1.1).

EXAMPLE 39

2β-Ethoxy-3α-hydroxy-21-morpholino-5α-pregnane-11,20-dione Citrate

A solution of 2β-ethoxy-3α-hydroxy-21-morpholino-5α-pregnane-11,20-dione (0.093 g, 0.2 mmole) in ethanol (1 ml) was treated with a 0.1M solution of citric acid (2 ml, 0.2 mmole) at room temperature. The clear solution was immediately evaporated to dryness at room temperature and redissolved in distilled water (ca. 5 ml). The aqueous solution was stored at 0° overnight and then filtered. The solid collected was washed with distilled water (ca. 1 ml) and the washings and filtrate combined. The residue was dissolved in chloroform and evaporated under vacuum to constant weight (0.0016 g). The filtrate and washings were made up to 9.14 ml with distilled water thereby giving a solution of title compound (pH 3.59) at concentration 10 mg/ml with respect to steroid.

EXAMPLE 40

21-Cyano-3α-hydroxy-19-nor-5α-pregnane-11,20-dione

21-Bromo-3α-hydroxy-19-nor-5α-pregnane-11,20-dione (794 mg.) was added to a solution of potassium cyanide (300 mg.) in ethanol (60 ml.) and water (5 ml.), and the mixture was refluxed for 1.5 hours. 2N-Sulphuric acid (5 ml.) was added, and the suspension was poured into water. The product was extracted with ethyl acetate and the combined extract was washed with water, dried (MgSO$_4$), and evaporated to yield a yellow foam. Purification by preparative tlc (CHCl$_3$/EtOAc 3:1) gave as the most polar constituent a yellow foam (400 mg.).

Further purification by preparative tlc (CHCl$_3$) afforded as the most polar component title compound (310 mg.) as a white foam, $[\alpha]_D + 178$ (c 0.9).

EXAMPLE 41

3α-Hydroxy-21-(cis and trans-2',6'-dimethylmorpholino-5α-pregnane-11,20-dione

21-Bromo-3α-hydroxy-5α-pregnane-11,20-dione (1 g.) was dissolved in dry tetrahydrofuran (50 ml.) and cis/trans-2,6-dimethylmorpholine (1 ml.) added to the solution. The mixture was refluxed for 4 hours. The mixture was poured into water, the emulsion extracted into ether, and the combined extracts washed with water, dried over anhydrous sodium sulphate and evaporated to a pale yellow foam (1.07 g.) which was purified by preparative T.L.C. in ethyl acetate. The faster running band (R$_f$~0.6) gave 3α-hydroxy-21-(trans-2',6'-dimethylmorpholino)-5α-pregnane-11,20-dione (150 mg., 14%) as a white foam. $[\alpha]_D + 70.5°$ (c 0.42).

A lower running band (R$_f$ 0.2 – 0.4) was removed in two sections giving products which were identical by spectroscopy. The initial foams were recrystallised from ethyl acetate/petrol to give 3α-hydroxy-21-(cis-2',6'-dimethylmorpholino)-5α-pregnane-11,20-dione (500 mg.) as off white needles, m.p. 134° (decomp.) $[\alpha]_D + 73.5°$ (c 1.06).

EXAMPLE 42

3α-Hydroxy-21-morpholino-5α-pregnane-11,20-dione hydrochloride

A solution of 3α-hydroxy-21-morpholino-5α-pregnane-11,20-dione (104.14 mg., 0.25 mmole) in ethanol (4 ml.) was treated with 0.1N hydrochloric acid (2.5 ml., 0.25 mmole). The solution was evaporated in vacuo and then treated with water (5 ml.). The undissolved solid (8.4 mg.) was removed by filtration and the filtrate was made up to 9.6 ml. with distilled water to give a 1% aqueous solution of the title compound.

EXAMPLE 43

3α-Hydroxy-21-morpholino-5α-pregnane-11,20-dione mesylate

A solution of 3α-hydroxy-21-morpholino-5α-pregnane-11,20dione (167 mg., 0.4 mmole) in ethanol (2 ml.) was treated with 0.204 N aqueous solution of methanesulphonic acid (3.92 ml. 0.8 mmole). The resulting solution was evaporated under vacuum and then treated with water (5 ml.). The undissolved solid (14.7 mg.) was removed by filtration and the filtrate was made up to 15.23 ml. with distilled water thereby obtaining a 1% aqueous solution of the title compound.

EXAMPLE 44

2β-Ethoxy-3α-hydroxy-21-morpholino-5α-pregnane-11,20-dione dihydrogen phosphate

2β-Ethoxy-3α-hydroxy-21-morpholino-5α-pregnane-11,20-dione (231.2 mg., 0.5 mmole) in ethanol (3 ml) was treated with 0.095M aq.orthophosphoric acid (5.3 ml., 1 equiv) and the resulting solution was evaporated, in vacuo. The residue was dissolved in water (5 ml) and made up to a total solution weight of 23.12 g. to give a 1% aqueous solution of the title compound.

EXAMPLE 45

3α-Hydroxy-21-thiamorpholino-19nor-5α-pregnane-11,20-dione citrate

3α-hydroxy-21-thiamorpholino-19nor-5α-pregnane-11,20-dione (83.922 mg. 0.2 mmole) was dissolved in ethanol (2 ml.) and a solution of citric acid (2 ml; 0.1M 10.507g/500 ml; 0.2 mmole) was added. The solution was evaporated to dryness, dissolved in water (5 ml.) and filtered. Insoluble material weighed 7 mg. The filtrate, water white, was assumed to contain steroidal base (76.9 mg.); the volume was adjusted to 7.69 ml. to give a solution of the title compound (10 mg/ml w.r.t. steroid base). The pH of the solution was 3.2.

EXAMPLE 46

2β-Ethoxy-3α-hydroxy-21-morpholino-5α-pregnane-11,20-dione acetate

A solution of 2β-ethoxy-3α-hydroxy-21-morpholino-5α-pregnane-11,20-dione (116 mg., 0.25 mmole) in ethanol (2 ml.) was treated with 0.1N aqueous acetic acid (2.5 ml. 0.25 mmole) and the resulting solution was evaporated under vacuum. The residue was treated with water (ca 1 ml.) and the undissolved solid (66 mg.) was removed by filtration. The filtrate was diluted to 5 ml. with distilled water, thereby giving a 1% aqueous solution of the title compound.

EXAMPLE 47

3α-Hydroxy-2-morpholinopregn-4-ene-11,20-dione

21-Bromo-3α-hydroxypregn-4-ene-11,20-dione (150 mg.) in tetrahydrofuran (5 ml.) was treated with morpholine (0.1 ml.) and the stirred mixture was refluxed under nitrogen for 2 hours, during which time a white precipitate formed. The mixture was partitioned between methylene chloride and water. The aqueous layer was extracted with more methylene chloride and the combined organic extracts were washed with water, dried over sodium sulphate and evaporated to a foam (152 mg.) which was purified by preparative T.L.C. in acetone/petrol 1/1, the main band Rf 0.3-0.45 being separated to give title compound (99 mg.) as a white foam, $[\alpha]_D + 174°$ (c 0.12)

EXAMPLE 48

3α-Hydroxy-21-morpholino-5α-pregnane-11,20-dione citrate

A solution of 3α-hydroxy-21-morpholino-5α-pregnane-11,20-dione (83.52 mg. 0.2 mmole) in absolute ethanol (1 ml.) was treated with 0.1M aqueous citric acid (2 ml. 0.2 mmole). The ethanol was removed by evaporation and the resulting solution freeze-dried. Water (5 ml.) was added, and the cloudy solution obtained left to stand at room temperature for two hours. The solution was filtered through a No. 3 sinter. The flask was rinsed with water (0.5 ml.) and this was also filtered. The sinter and flask were washed with chloroform (10 ml.). The chloroform was washed with saturated sodium bicarbonate solution (2 × 5 ml.) and with water (3 × 5 ml.) and evaporated to a residue which was dried by azeotroping with benzene (6 × 10 ml.) and in vacuo (20.6 mg.). The filtrate waas diluted with water (1 ml.) to give title compound as a 10 mg./ml. aqueous solution with respect to steroid. The pH of the solution was 3.45.

EXAMPLE 49

2β-Ethoxy-3α-hydroxy-21-morpholino-5α-pregnane-11,20-dione ascorbate

A solution of 2β-Ethoxy-3α-hydroxy-21-morpholino-5α-pregnane-11,20-dione (116 mg; 0.25 mmole) in ethanol (2 ml.) was treated with an 0.1N aqueous solution of ascorbic acid (2.5 ml; 0.25 mmole) and the resulting solution was evaporated under vacuum. The residue was dissolved in water (ca. 5 ml.) and clarified by filtration. The filtrate was diluted to 11.6 ml. with distilled water, thereby giving a 1% aqueous solution of the title compound.

EXAMPLE 50

3α-Hydroxy-21-morpholino-5α-pregnane-11,20-dione

A solution of 21-morpholino-5α-pregnane-3,11,20-trione (100 mg.) in the "stock" hloroiridic solution (see preparation 6 below) (10 ml.), was refluxed for 14 hours. The cooled mixture was poured into water and made just alkaline. The slight oily precipitate was extracted into ethyl acetate and the extracts were washed with water, dried ($Na_2SO_4$), and evaporated to give essentially the title compound, shown by n.m.r. spectroscopy and T.L.C. (Rf 0.16) on silica in ethyl acetate to be identical to the product of Example 38.

EXAMPLE 51

3α-Hydroxy-21-morpholino-5α-pregnane-11,20-dione

21-Chloro-5α-pregnane-3,11,20-trione (200 mg.) in dry tetrahydrofuran (4 ml.) was treated with morpholine (0.20 ml.), and the solution was refluxed for 2½ hours, and then left at room temperature for 3 days. The solution was diluted with water and extracted with chloroform. The organic solution was washed with water, dried over sodium sulphate and evaporated to a white foam (210 mg.), which was purified by preparative TLC in ethyl acetate to give 21-morpholino-5α-pregnane-3,11,20-trione (88 mg.) as a white foam, $[\alpha]_D + 99°$, (c 0.59). Treatment of this product in similar manner to that described in Example 50 gave title compound.

EXAMPLE 52

2β-Ethoxy-3α-hydroxy-21-morpholino-5α-pregnane-11,20-dione citrate (partial salt solution)

A solution of 2β-ethoxy-3α-hydroxy-21-morpholino-5α-pregnane-11,20-dione (0.93 g.) in ethanol (1 ml.) was treated with a 0.1 M solution of citric acid (20 ml.) at room temperature. The solution was evaporated to dryness and redissolved in distilled water (5 ml.). The resulting solution was filtered and the collected residue was washed with water (1 ml.). The filtrate and washings were made up to 9.2 ml with distilled water thereby giving a solution of 2β-ethoxy-3α-hydroxy-21-morpholino-5α-pregnane-11,20-dione citrate at concentration 100 mg./ml. with respect to steroid (pH 3.5).

To this solution was added a further quantity of 2β-ethoxy-3α-hydroxy-21-morpholino-5α-pregnane-11,20-dione (0.93 g.) and the solution was clarified by filtration to give title solution (pH 3.9).

EXAMPLE 53

3α-Hydroxy-21-morpholino-5α-pregnane-11,20-dione citrate

3α-Hydroxy-21-morpholino-5α-pregnane-11,20-dione (500 mg) in ethanol (60 ml) was treated with N/10 aqueous citric acid (12 ml) and the mixture was evaporated to dryness. The residue was dried in vacuo to constant weight and the resultant solid dissolved in water (30 ml). The solution was filtered and the solid collected (1 mg) and discarded. Water was added to the filtrate until a concentration of 10 mg/ml with respect to steroid was obtained. The pH of this solution was 3.4. 2N-Aqueous sodium hydroxide was added dropwise until a pH of 4.7 was achieved.

FORMULATIONS

Example A 0.139 g of 3α-hydroxy-21-azido-5α-pregnane-11,20-dione were dissolved in 2 ml of acetone at 20°C. The resulting solution was added to a 1 g of Cremophor EL at 20°C and stirred until homogeneous. The acetone was removed by a vigorous stream of nitrogen. The solution was diluted with sterile distilled water containing 0.025 g of sodium chloride to give a final volume of 5 ml.

Example B 0.025 g of 2β-ethoxy-3α-hydroxy-21-azido-5α-pregnane-11,20-dione were dissolved in 2 ml of acetone at 20°C. The resulting solution was added to 1 g of Cremophor EL at 20°C and stirred until homogeneous. The acetone was removed by a vigorous stream of nitrogen. The solution was diluted with sterile distilled water containing 0.025 g of sodium chloride to give a final volume of 5 ml.

Example C 0.009 of 3α-hydroxy-21-azido-5α-pregnan-20-one were dissolved in 2 ml of acetone at 20°C. The resulting solution was added to 2 g of Cremophor EL at 20°C and stirred until homogeneous. The acetone was removed by a vigorous stream of nitrogen. The solution was diluted with sterile distilled water containing 0.05 g of sodium chloride to give a final volume of 10 ml.

PREPARATION 1

21-Bromo-3α-hydroxy-5β-pregnane-11,20-dione

A stirred solution of 3α-hydroxy-5β-pregnane-11,20-dione (10 g.) in dry methanol (700 ml.) was treated at 0° with a solution of bromine (1.9 ml.) in methanol (45 ml.) at such a rate that the yellow colour disappeared before further addition. The solution was then partitioned between water and chloroform. The organic layer was washed with water, dried ($Na_2SO_4$) and evaporated. Chromatography of the residue (with benzene/ethyl acetate, 2.5:1) gave title compound (7.2 g.) as a white foam; $[\alpha]_D + 100°$(c 1.1).

PREPARATION 2

21-Bromo-3α-hydroxy-19-nor-5α-pregnane-11,20-dione

A solution of 3α-hydroxy-19-nor-5α-pregnane-11,20-dione (5.0 g.) in dry methanol (300 ml.) was stirred at 0°–5° during the dropwise addition of bromine (0.82 ml.) in methanol (20 ml.). After 1 hour the reaction was extremely slow (as indicated by removal of bromine colouration before further addition). External cooling was removed and hydrobromic acid (1 drop) was added. Further addition of bromine resulted in rapid decolouration and the reaction was completed in a further 1.5 hours. The reaction mixture was partitioned between ethyl acetate and water, washed with water, dried (MgSO$_4$) and evaporated to give a white foam (6.2 g.). Isolation of the main band after preparative t.l.c. (EtOAc) gave 90% pure title compound (5.2 g.)

PREPARATION 3

11α-Hydroxy-19-norpregna-4,16-diene-3,20-dione

A solution of a mixture of 11α,17α-dihydroxy-19-norpregn-4-ene-3,20-dione (4 g.) and semicarbazide hydrochloride (4 g.) in methanol (200 ml.) was refluxed for 2 hours. The methanol was then removed by distillation under reduced pressure and water was added to the residue. The precipitated solid was collected by filtration, washed with water and dried over P$_2$O$_5$ in vacuo. A solution of this solid in a mixture of glacial acetic acid (80 ml.), water (28 ml.) and pyruvic acid (4 ml.) was heated on a steam bath for 1 hour. The resulting solution was concentrated under reduced pressure and partitioned between saturated aqueous sodium bicarbonate and ethyl acetate. The organic layer was washed with water, dried (Na$_2$SO$_4$) and evaporated to dryness. The residue was subjected to preparative t.l.c. (CHCl$_3$/(CH$_3$)$_2$ CO; 15 : 1) and crystallised from acetone/petrol to afford title compound (1.6 g.) as white needles, m.p. 149°.

PREPARATION 4

19-nor-5α-pregna-3,11,20-trione via 3ξ, 11α,20ξ-trihydroxy-19-nor-5α-pregnane

A solution of 11α-hydroxy-19-norpregna-4,16-diene-3,20-dione (2.5 g.) in dry tetrahydrofuran (200 ml.) was added over 5 mins. to a solution of lithium (5 g.) in liquid ammonia (2.5 liters). The solution was then left for 30 min. Ethanol (ca. 100 ml.) was then added until the blue colour had been discharged and the ammonia was then allowed to evaporate. The residue was partitioned between water and ether. The organic layer was washed, dried (Na$_2$SO$_4$) and evaporated to give crude title compound (1.5 g.).

PREPARATION 5

19-Nor-5α-pregnane-3,11,20-trione

A solution of crude 3ξ,11α,20ξ-trihydroxy-19-nor-5α-pregnane (4 g.) in acetone (280 ml.) was treated with a solution of potassium dichromate (8.0 g.) in 2N-sulphuric acid (38 ml.) at room temperature for 1 hr. An additional quantity of potassium dichormate (8 g.) in 2N-sulphuric acid (38 ml.) was then added and left at room temperature for 15 mins. The solution was then partitioned between water and ether and the organic layer was washed with water, dried (Na$_2$SO$_4$) and evaporated. The residual oil was subjected to preparative t.l.c. (CHCl$_3$) and recrystallised from acetone/petrol to afford title compound (1.04 g.) as white prisms, m.p. 151°, [α]$_D$ + 240°.

PREPARATION 6

3α-Hydroxy-19-nor-5α-pregnane-11,20-dione

A solution of 19-nor-5α-pregnane-3,11,20-trione (0.9 g.) in "stock" chloroiridic solution [prepared by refluxing a mixture of chloroiridic acid (0.09 g.) 90% isopropyl alcohol (200 ml.) and trimethyl phosphite (16 ml.) for 16 hr. The solution was neutralised with triethylamine immediately prior to use], (75 ml.) was refluxed for 24 hr. The solution was then cooled, partitioned between water and ether and the organic layer was washed well with water, dried (Na$_2$SO$_4$) and evaporated. The residue was subjected to preparative t.l.c. (EtOh) and recrystallised from acetone to afford title compound (0.6 g.) as white needles, m.p. 154°, [α]$_D$ + 200°.

PREPARATION 7

21-Bromo-3α-hydroxy-3β-methyl-5α-pregnane-11,20-dione

A stirred solution of 3α-hydroxy-3β-methyl-5α-pregnane-11,20-dione (17) (5.0 g., 15.0 mmole) in methanol (300 ml.) was treated with a solution of bromine (1.0 ml.) in methanol (30 ml.) at 0° and at such a rate that the yellow colour of the solution disappeared before further addition of the bromine solution took place. The mixture was then poured into water; the precipitated title compound (2.8 g.) was collected by filtration and dried over P$_2$O$_5$ in vacuo.

PREPARATION 8

21-Bromo-3α-hydroxy-2β-methoxy-5α-pregnan-20-one

A stirred solution of 3α-hydroxy-2β-methoxy-5α-pregnan-20-one (4.0 g.) in dry methanol (300 ml.) was treated at 0° with a solution of bromine (0.65 ml.) in methanol (15 ml.) at such a rate that the yellow colour disappeared before further addition. The mixture was then poured into water and the precipitated solid was collected by filtration, washed with water and dried in vacuo to give title compound (4.0 g) as white crystals.

PREPARATION 9

21-Bromo-3α-hydroxy-2β-methyl-5α-pregnane-11,20-dione

A solution of 3α-hydroxy-2β-methyl-5α-pregnane-11,20-dione (1.04g.) in dry methanol (150ml) was stirred at 0°–5° during the dropwise addition of a solution of bromine (0.16ml) in dry methanol (20ml) over a period of 2.5 hours. The reaction mixture was partitioned between ethyl acetate and water and the organic layer was separated, washed with water, dried (MgSO$_4$) and evaporated to a white foam; purification by preparative t.l.c. (ethyl acetate: benzene 1:2.5) gave the title compound (510mg.), m.p. 140° dec.; [α]$_D$ + 133° (c 0.95).

PREPARATION 10

21-Bromo-2β-ethoxy-3α-hydroxy-5α-pregnane-11,20-dione

Bromine (0.53 g.) in methanol (1.45 ml.) was added dropwise to a stirred solution of 3α-hydroxy-2β-ethoxy-5α-pregnane-11,20-dione (2.0 g) in methanol (15 ml) containing a trace of acetyl chloride at 0°. The addition took 2 hr. and the clear solution was then poured into water and collected by filtration, washed with water and dried in vacuo to give title compound.

PREPARATION 11

21-Bromo-3α-hydroxy-2β-n-propoxy-5α-pregnane-11,20-dione

A solution of 3α-hydroxy-2β-n-propoxy-5α-pregnane-11°-dione (2.0 g.) in methanol (15 ml.) was treated dropwise during 2 hr. with a solution of bromine in methanol (2.5 ml. of a solution containing 0.314 gm/ml. of bromine). The resulting solution was then poured into water and the precipitated solid was collected by filtration, washed with water and dried in vacuo to give title compound

PREPARATION 12

21-Bromo-5α-pregnane-3,11,20-trione

21-Bromo-3α-hydroxy-5α-pregnane-11,20-dione (412 mg) in acetone (20 ml) was stirred during dropwise addition of Jones reagent (0.4 ml) at room temperature. After 10 minutes, the reaction mixture was poured onto water extracted with chloroform and the combined chloroform extract was washed with water dried ($MgSO_4$) and evaporated. The residue was crystallised from ether/petrol to give title compound (350 mg) as white microcrystals mp 170° $[\alpha_D] + 132°$ (ε 1.1).

Jones reagent refers to a solution of chromium trioxide (267g) in a mixture of concentrated sulphuric acid (230 ml) and water (400 ml) made up to 1 liter with water (8N w.r.t. oxygen). Stock chloroiridic solution was prepared by refluxing a mixture of chloroiridic acid (0.09g), 90% isopropanol (200 ml) and trimethyl phosphite (16 ml) for 16 hours. The solution was neutralised with triethylamine immediately prior to use.

PREPARATION 13

21-Morpholino-5α-pregnane-3,11,20-trione

A solution of 21-bromo-5α-pregnane-3,11,20-trione (500 mg) in dry tetrahydrofuran was treated at reflux with morpholine (0.5 ml) for ½ hour, and poured into water. The oily precipitate was extracted into ether and the extracts were washed with water, dried ($Na_2SO_4$) and evaporated to the crude product which was purified by preparative t.l.c. in ethyl acetate and crystallisation from ether to give the title compound (220 mg). m.p. 159°–164°C $[\alpha]_D$ +98° (c=1.1%)

PREPARATION 14

21-Bromo-3α-hydroxy-5α-pregn-1-ene-11,20-dione

A stirred solution of 2β-bromo-3α-hydroxy-5α-pregnane-11,20-dione (5.0 g.) in methanol (100 ml.) was treated at 0° with a solution of bromine (1 ml.) in methaol (30 ml.) at such a rate that the yellow colour disappeared before further addition of the bromine solution. The mixture was then poured into water and the precipitated solid was collected by filtration, washed with water and dried over $P_2O_5$ in vacuo. The resulting solid (5.0 g.) was purified by column chromatography (silica, EtOAc/ $C_6H_6$ 1:2.5) to give crude 2β,21-dibromo-3α-hydroxy-5α-pregnane-11,20-dione (3,4 g.).

A solution of crude 2β,21-dibromo-steriod (2.0 g.) in benzene (100 ml.) was treated with dihydropyran (2 ml.) and p-toluenesulphonic acid (40 mg.) for 20 minutes. The reaction mixture was then washed successively with dilute aqueous sodium bicarbonate and water, dried ($Na_2SO_4$) and evaporated. The residue was subjected to preparative t/c ($CHCl_3$) to give slightly crude 2β,21-dibromo-3α-tetrahydropyranoxy-5α-pregnane-11,20-dione as a white foam.

A mixture of this product (0.7 g.) dimethylacetamide (20 ml.), lithium bromide (2.6 g.) and calcium carbonate (4.0 g.) was stirred at 100° for 2 hours. The calcium carbonate was then removed by filtration and the filtrate was partitioned between ether and water. The organic layer was wahed with water, dried ($Na_2SO_4$) and evaporated.

A solution of the residue (0.5 g.) in ethaol (5 ml.) was stirred at room temperature with 2N-hydrochloric acid (0.5 ml.) for 2 hours. The mixture was then partitioned between aqueous sodium bicarbonate and ether. The organic layer was washed with water, dried ($Na_2SO_4$) and evaporated. The residue was subjected to preparative tlc (EtOAc/$CHCl_3$, 1:2) to give title compound (0.15 g.) as a white foam $[\alpha]_D + 85°$ (c 0.8).

PREPARATION 15

N-(2'-hydroxy-2'-phenylethyl)-ethanolamine

Styrene oxide (1.2 g.), ethanolamine (0.6 g.) and water (0.05 g.) were heated at 70° with stirring for 24 hours. The mixture was cooled, evacuated and the oil formed triturated with ether to give title compound (550 mg.) m.p 93.5° – 95°.

PREPARATION 16

2-Phenylmorpholine

N-(2'-hydroxy-2'-phenylethyl)-ethanolamine (5.3 g.) was dissolved in 6N hydrochloric acid (100 ml.) and the solution heated at 110° for 4 hours. The mixture was basified with sodium hydroxide solution and extracted into ether. The extract was washed with water, dried over anhydrous sodium sulphate and evaporated to give a crude sample of title compound (1g.) as an orange oil.

PREPARATION 17

4β,21-Dibromo-3α-hydroxy-5α-pregnane-11,20-dione

4β-Bromo-3α-hydroxy-5α-pregnane-11,20-dione (945 mg) in dry methanol (70 ml.) at 10° was treated with a solution of bromine (0.125 ml.) in methanol (5 ml.) dropwise over 7 hours, at such a rate that the bromine colour was taken up during the addition. The reaction solution was then stirred at room temperature for 30 minutes until it became colourless, and it was then diluted with water (300 ml.) and the white precipitate was extracted into methylene chloride. The organic solution was washed with water, dried over sodium sulphate and evaporated to a white foam (1.2 g.) which was purified by preparative T.L.C. in ethyl acetate/benzene ⅓ the upper (major) band giving 660 mg. of a white solid which was triturated with ether to give title compound (580 mg.) as white crystals, m.p. 164°–166°, $[\alpha]_D + 76°$ (c 1.35).

PREPARATION 18

21-Bromo-3α-hydroxypregn-4-ene-11,20-dione

4β,21-Dibromo-3α-hydroxy-5α-pregnane-11,20-dione (200 mg.) in dry dimethyl acetamide (10 ml.) was treated with calofort U (1.5 g.) and lithium bromide (0.9 g.). The mixture was stirred at 85° for 3½ hours. The reaction mixture was filtered, and the solid residue was washed with ether and ethyl acetate. The combined filtrate and washings were washed well (5 times) with water, dried over sodium sulphate and evaporated to a brown oil which was purified by preparative T.L.C. in ethyl acetate/petrol 1/1, the main band yielding title compound (70 mg.) as a colourless foam, $[\alpha]_D + 140°$.

The preparations of other intermediates necessary for the preparations described in the Examples are given in U.S. patent application Ser. Nos. 208,961 and 19,715.

PREPARATION 19

21-Hydroxy-5α-pregnane-3,11,20-trione

21-Acetoxy-5α-pregnane-3,11,20-trione (4.85 g.) in hot methanol (200 ml.) was treated with potassium bicarbonate solution (10%; 20 ml.) and the stirred solution was refluxed under nitrogen for 15 minutes. The cooled reaction mixture was diluted with water and the oily precipitate was extracted into methylene chloride. The extract was washed with water, dried over sodium sulphate and evaporated to a foam (4.3 g.) which was triturated with ether to give title compound (3.07 g.) as white crystals, m.p. 164°–170°.

PREPARATION 20

21-Chloro-5α-pregnane-3,11,20-trione

21-Hydroxy-5α-pregnane-3,11,20-trione (3.0 g.) in anhydrous pyridine (15 ml.) was treated with toluene-4-sulphonyl chloride (3.0 g.) and the pale orange solution was stirred at room temperature for 3 hours. The cold solution was vigorously stirred during the slow addition of ice-cold water (200 ml.) and hydrochloric acid (2N;50 ml.). The yellow crystalline precipitate was filtered off, washed well with water and dried in vacuo at 60°, and the resulting crude product (2.4 g.) was recrystallized from acetone/petrol to give crude title compound (1.13 g.) as an off-white crystalline solid, m.p. 168°–172°, $[\alpha]_D + 137°$ (c 1.13).

We claim:

1. A steroid compound of the formula or a pharmaceutically acceptable salt thereof wherein
$R^1$ is —H or —CH$_3$;
$R^2$ is H, C$_1$–C$_6$ alkyl or a halogen atom;
$R^3$ is H, acyloxy or acylthio of 1–9 C atoms, an ether or thioeter group of 1–9 C atoms, an alkyl or cycloalkyl group of up to 9 C atoms, phenyl, benzyl, hydroxy, thiocyanato, nitrooxy, a halogen atom, azido, amino, monoalkylamino, dialkylamino or morpholino;
$R^4$ is H or C$_1$–C$_6$ alkyl;
$R^5$ and $R^6$ are each H, C$_1$–C$_6$ alkyl, C$_1$–C$_6$ alkoxy or a halogen atom, only one of $R^5$ and $R^6$ being a halogen atom;
$R^7$ is cyano, azido or substituted or unsubstituted morpholino, thiamorpholino, pyrrolino, pyrrolidino, piperidino or thiazolidino; and
X is oxo, an epoxy group linked also to the 9-position or a grouping wherein $R^8$ is H, hydroxy or alkyl or alkenyl of up to 6 C atoms and $R^9$ is H or hydroxy, only one of $R^8$ and $R^9$ being hydroxy, the lines $===$ indicating the presence of a single or double bond at the $\Delta^1$, $\Delta^4$ and $\Delta^{8(9)}$ positions.

2. A steroid as claimed in claim 1 which possesses a 5α-hydrogen atom.

3. A steroid as claimed in claim 1 which possesses an 11-oxo group.

4. A steroid as claimed in claim 1 which possesses at least one of a 16α-methyl group, a double bond at the $\Delta^1$ or $\Delta^4$ position and a 2β-alkyl or alkoxy group.

5. A steroid as claimed in claim 1 wherein $R^7$ is a morpholino or thiamorpholino group.

6. A steroid as claimed in claim 1 wherein $R^7$ is morpholino, thiamorpholino, pyrrolino, pyrrolidino, piperidino or thiazolidino substituted by at least one alkyl substituent.

7. A steroid as claimed in claim 1 wherein $R^7$ is a thiazolidino group.

8. A steroid as claimed in claim 1 which possesses a basic nitrogen atom and is in the form of its hydrochloride, hydrobromide, phosphate, sulphate, p-toluenesulphonate, methanesulphonate, citrate, tartrate, acetate, ascorbate, lactate, maleate or succinate.

9. A steroid as claimed in claim 1 which possesses a 21-cyano group and is in the form of a salt with a base.

10. The steroid of claim 1 which is 21-cyano-3α-hydroxy-5α-pregnane-11,20-dione or its sodium salt; 21-cyano-2β-ethoxy-3α-hydroxy-5α-pregnane-11,20-dione or its sodium salt; 21-cyano-2β-methoxy-3α-hydroxy-5α-pregnane-11,20-dione; 21-cyano-2β-isopropoxy-3α-hydroxy-5α-pregnane-11,20-dione; 21-cyano-3α-hydroxy-16α-methyl-5α-pregnane-11,20-dione; 3α-hydroxy-21-morpholino-5α-pregnane-11,20-dione or its citrate, mesylate or hydrochloride; 2β-ethoxy-3α-hydroxy-21-morpholino-5α-pregnane-11,20-dione or its citrate, phosphate, acetate or ascorbate; 3α-hydroxy-16α-methyl-21-morpholino-5α-pregnane-11,20-dione; 3α-hydroxy-21-(2'-methylmorpholino)-5α-pregnane-11,20-dione; 3α-hydroxy-21-(cis-2',6'-dimethylmorpholino)-5α-pregnane-11,20-dione; 3α-hydroxy-21-thiamorpholino-19-nor-5α-pregnane-11,20-dione or its citrate; 21-azido-3α-hydroxy-5α-pregnane-11,20-dione; 21-azido-2β-ethoxy-3α-hydroxy-5α-pregnane-11,20-dione; 21-azido-3α-hydroxy-5β-pregnane-11,20-dione; 21-azido-3α-hydroxy-5α-pregnan-20-one; 21-azido-3α-hydroxy-16α-methyl-5α-pregnane-11,20-dione; 21-azido-3α-hydroxy-2β-methoxy-5α-pregnan-20-one; 21-azido-3α-hydroxy-19-nor-5α-pregnane-11,20-dione; or 21-azido-3α-hydroxy-5α-pregn-1-ene-11,20-dione.

11. The steroid of claim 1 which is 21-cyano-3α-hydroxy-2β-methyl-5α-pregnane-11,20-dione; 3α-hydroxy-21-thiazolidino-5α-pregnane-11,20-dione; or 21-azido-3α-hydroxy-2β-methyl-5α-pregnane-11,20-dione.

12. A steroid as claimed in claim 1 wherein R⁷ is a morpholino group.

13. The steroid of claim 1 which is 21-cyano-3α-hydroxy-5α-pregnane-11,30-dione or the sodium salt thereof.

14. The steroid of claim 1 which is 21-cyano-2β-ethoxy-3α-hydroxy-5α-pregnane-11,20-dione or the sodium salt thereof.

15. The steroid of claim 1 which is 21-cyano-2β-methoxy-3α-hydroxy-5α-pregnane-11,20-dione.

16. The steroid of claim 1 which is 3α-hydroxy-21-morpholino-5α-pregnane-11,20-dione or the citrate, mesylate or hydrochloride salt thereof.

17. The steroid of claim 1 which is 2β-ethoxy-3α-hydroxy-21-morpholino-5α-pregnane-11,20-dione or the citrate, phosphate, acetate or ascorbate salt thereof.

18. The steroid of claim 1 which is 3α-hydroxy-16α-methyl-21-morpholino-5α-pregnane-11,20-dione.

19. The steroid of claim 1 which is 3α-hydroxy-21-(cis-2',6'-dimethylmorpholino)-5α-pregnane-11,20-dione.

20. The steroid of claim 1 which is 3α-hydroxy-21-thiamorpholino-19-nor-5α-pregnane-11,20-dione or the citrate salt thereof.

21. The steroid of claim 1 which is 21-azido-3α-hydroxy-5α-pregnane-11,20-dione.

22. The steroid of claim 1 which is 21-azido-2β-ethoxy-3α-hydroxy-5α-pregnane-11,20-dione.

23. The steroid of claim 1 which is 21-azido-3α-hydroxy-5α-pregnan-20-one.

24. The steroid of claim 1 which is 21-azido-3α-hydroxy-2β-methoxy-5α-pregnan-20-one.

25. The steroid of claim 1 which is 21-azido-3α-hydroxy-5α-pregn-1-ene-11,20-dione.

26. The steroid of claim 1 which is 3α-hydroxy-21-thiazolidino-5α-pregnane-11,20-dione.

27. A steroid compound of the formula

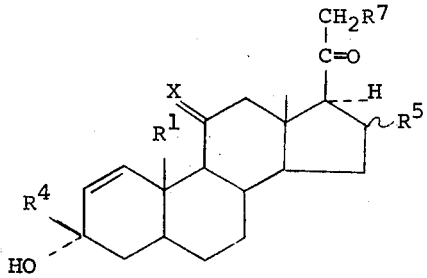

or a pharmaceutically acceptable salt thereof wherein
R¹ is —H or —CH₃;
R⁴ is —H or —CH₃;
R⁵ is two hydrogen atoms or a hydrogen atom and methyl in the α- or β-configuration or gem-dimethyl;
R⁷ is cyano, azido, morpholino, thiamorpholino; pyrrolino, pyrrolidino, peperidino or thiazolidino; and
X is two hydrogen atoms or oxo.

28. A steroid compound of the formula

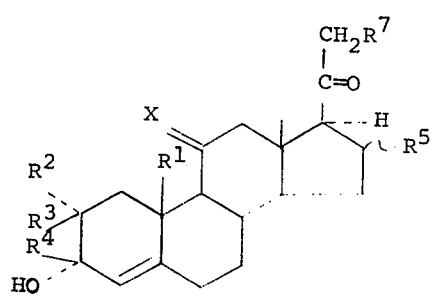

or a pharmaceutically acceptable salt thereof wherein
R¹ is —H or —CH₃;
R² is —H or —CH₃;
R³ is —H, C₁₋₅ alkyl, C₁₋₆ alkoxy, C₂₋₆ alkanoyloxy, a halogen atom or thiocyanato, R² being —CH₃ only when R³ is H;
R⁴ is —H or —CH₃;
R⁵ is two hydrogen atoms or a hydrogen atom and methyl in the α- or β-configuration or gem-dimethyl;
R⁷ is cyano, azido, morpholino, thiamorpholino; pyrrolino, pyrrolidino, peperidino or thiazolidino; and
X is two hydrogen atoms or oxo.

* * * * *